United States Patent [19]

Feriani et al.

[11] Patent Number: 4,630,727
[45] Date of Patent: Dec. 23, 1986

[54] CONTAINER FOR A BICARBONATE CONTAINING FLUID

[75] Inventors: Mariano Feriani, Arcugnano; Stefano Biasioli, Vicenza, both of Italy

[73] Assignee: Fresenius, AG, Fed. Rep. of Germany

[21] Appl. No.: 719,903

[22] Filed: Apr. 4, 1985

[30] Foreign Application Priority Data
Apr. 6, 1984 [IT] Italy .............................. 85554 A/84

[51] Int. Cl.⁴ ............................................. B65D 81/32
[52] U.S. Cl. .................................. 206/221; 206/484; 206/524.2; 604/416
[58] Field of Search ............... 206/216, 219, 221, 438, 206/484, 524.1, 524.2, 524.6, 568; 604/403–416

[56] References Cited

U.S. PATENT DOCUMENTS

| 4,132,594 | 1/1979 | Bank et al. | 604/408 |
| 4,282,863 | 8/1981 | Beigler | 206/219 |
| 4,396,383 | 8/1983 | Hart | 604/416 |
| 4,458,733 | 7/1984 | Lyons | 206/219 |
| 4,458,811 | 7/1984 | Wilkinson | 206/219 |
| 4,467,588 | 8/1984 | Carveth | 604/410 |
| 4,484,920 | 11/1984 | Kaufman et al. | 604/416 |
| 4,496,361 | 1/1985 | Kilkson | 604/408 |
| 4,516,977 | 5/1985 | Herbert | 604/408 |

Primary Examiner—William Price
Assistant Examiner—Jimmy G. Foster
Attorney, Agent, or Firm—Omri M. Behr

[57] ABSTRACT

A twin-chamber bag (10) is made in the form of a first chamber (12), that is filled with a bicarbonate-containing fluid (34) and a second chamber (14), that is filled with an acid fluid (36). The two chambers (12 and 14) are joined by way of a passage (20) that is blocked up till the time the bag is to be used to prevent mixing of the fluids.

19 Claims, 3 Drawing Figures

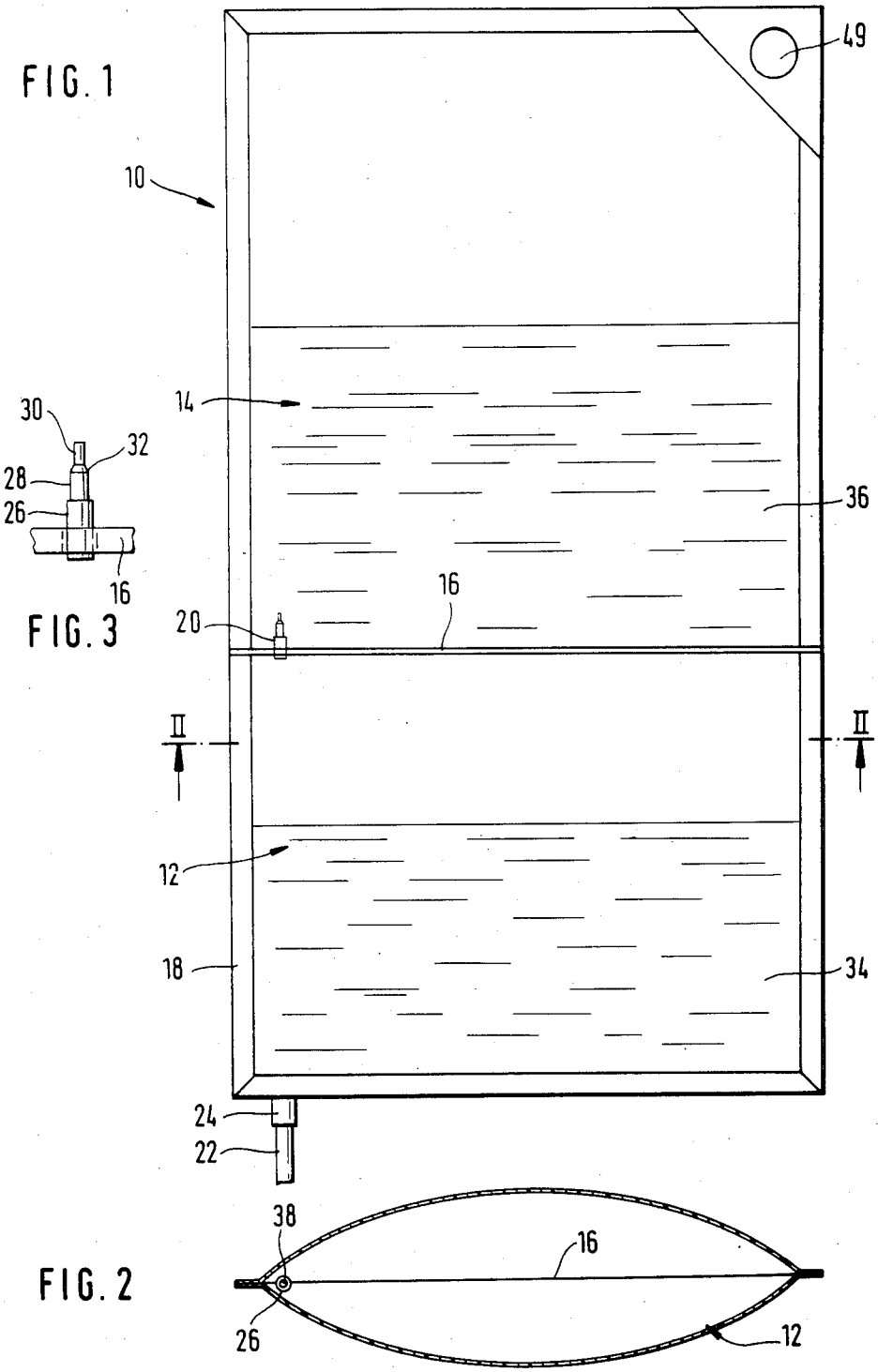

CONTAINER FOR A BICARBONATE CONTAINING FLUID

The invention relates to a container for preparing a bicarbonate containing solution for dialysis, substitution or infusion for peritoneal dialysis, hemofiltration and the like, having a first container part filled with acid solution, and a second container part separated from the first one by a flow blocking valve which is filled with a bicarbonate-containing solution, one of said container parts having at least one discharge tube having a removable closure.

For continuous ambulant peritoneal dialysis (CAPD) a dialysing fluid is introduced into the peritoneal cavity, the fluid having the necessary electrolyte combination for dialysis and containing acetate or lactate ions as a buffer element for countering metabolic acidosis. Such a liquid is however weakly acid and inhibits the antimicrobial bodies present in the peritoneum so that the introduction of such solution into the peritoneal cavity has to be under strictly aseptic condition as otherwise there would be a risk of peritonitis.

On this basis attempts have already been undertaken to produce bicarbonate-containing solutions for peritoneal dialysis in order to create conditions in the peritoneum as well which are as physiological as possible, one result then being that there is no longer the inhibition of the antimicrobial bodies.

In this respect there has been a proposal, for example in the European Pat. No. 22,922 to use a bicarbonate-containing dialysis fluid produced by mixing an acid concentrate with a bicarbonate concentrate with the addition of water. In this respect two concentrates have to be used, as there would otherwise be the danger of a reaction between calcium ions with carbonate ions to give insoluble calcium carbonate which would then not be available for physiological requirements.

Such solutions were however not sufficiently sterile for introduction into the peritoneal cavity and further developments were necessary.

In this connection T. S. Ing. et al in Int. J. Artif. Organs 1981, pages 308 and 309 and 1983 pages 217 and 218 described the on-line production of a bicarbonate-containing dialysis fluid for use in peritoneal dialysis with an acid solution that is mixed with a basic one to produce the dialysate product for administration to the patient. In this case the basic solution, which contains the sodium bicarbonate is generally held in a glass vessel, as for example a glass bottle or a syringe of glass, in which there is generally speaking no danger of evolution and loss of carbon dioxide from the bicarbonate during a long shelf life. Consequently the bicarbonate-containing solution as originally packed remains intact in the glass vessel and is therefore fully available for the production of the bicarbonate-containing dialysis solution.

Medicinal solutions must as a rule have a shelf life of at least one year and have to be stable, or in other words, during this time there is to be no alteration of the composition of such fluid. The bicarbonate ion is however in equilibrium between the $OH^-$ ion and $CO_2$ that, although it may be dissolved physically in the aqueous solution, may furthermore be lost from the container if there is any possibility of such diffusion from it. In addition decomposition of the bicarbonate and the release of $CO_2$ cause an internal pressure in the container that means that the container has to have a certain degree of strength such that it will not burst.

In this connection Ing et al therefore proposed a glass container for use with their bicarbonate-containing solution of the type normally used for packaging $CO_2$ aerated mineral waters.

The use of such a device is however not suitable for CAPD, because usually the container has to be in the form of a bag carried on the body of the patient and used for dispensing the fresh dialysis fluid through a system of hoses into the peritoneal cavity and for receiving spent dialysis fluid.

Therefore one object of the present invention it to devise a container of the initially stated sort that it may be used in CAPD, hemofiltration or infusion without any problems and more specially without any danger in practice of the bicarbonate-containing solution undergoing any alteration.

In order to effect this and other purposes the first and second container parts are placed in a bag structure having at least two chambers and made of an organic polymer.

It surprisingly has been discovered that the container in accordance with the invention may be used prolonged long-term storage of bicarbonate-containing solutions, that is to say, in practice there is no danger of $CO_2$ evolved through the decomposition of bicarbonate diffusing through the polymeric wall of the bag. This is unexpected inasfar as it had always been assumed so far that it was necessary to either use thick-walled plastics or gas-tight glass containers in order effectively to prevent diffusion of the released $CO_2$.

The invention makes it possible for the first time to use a bag for bicarbonate-containing solutions, which assures a sufficient shelf life, that it to say guarantees a storage time of at least one year for the originally produced bicarbonate solution without decomposition thereof.

Furthermore, the bag arrangement of the invention is particularly useful in connection with CAPD, since the bicarbonate-containing dialysis solution may be produced right before the introduction into the peritoneal cavity and thereafter the complete bag package may be comfortably worn on the body of the patient. This yields advantages both for the convenience of administration and also for the conduct of the CAPD operation itself from the medical aspect, because on the one hand the patient himself is independent of a dialysing machine and on the other hand the bicarbonate-containing dialysing fluid has the desired physiological pH value that does not inhibit the natural defense mechanism of the peritoneum.

It is furthermore to be noted that precipitation of calcium carbonate is prevented by the use of the bag of the present invention and that the solutions held therein may be formulated and sterilized without any difficulty and furthermore may be stored for the desired period of time in the plastics material employed.

In the container of the invention there are at least two container parts or compartments, that are joined together by way of a passage allowing flow of liquid. This passage part is normally in the form of a tube and may be rigid or soft and flexible in nature.

In the case of a rigid construction of the flow passage use will normally be made of a plastics tube made of a stiff material, that has its ends joined with the respective container parts. On the other hand the it is however possible to have such a passage part completely surrounded by the plastics material of the two compartments, this being especially advantageous.

Along the same lines it is however also possible to employ a flexible piece of tube, as for example in the form of a length of hose, that is joined with the respective container parts, as for example by welding. Such a flexible piece of hose may, like the rigid flow passage part, be connected either completely or in part with the respective plastics material of the two container parts.

Prior to the mixing of the two solutions contained in the two container parts the said flow passage is blocked and in accordance with the invention, is provided with a valve, that is opened or removed when the bag is to be used.

Such a valve or closure means may for example be in the form of the normally used frangible parts in the case of the rigid embodiment of the invention, such parts shutting off a tubular member and being broken off for use along a line of weakness from this tubular part. In this respect it is here a question of a valve integrally joined to the two container parts, that is best provided on the flow passage part that is also integrally joined to the two container parts.

Furthermore it is naturally possible for the flow passage part to have a barrier wall, that is broken directly prior to use so that the flow passage therethrough is unblocked. In this regard it is possible for example again to employ a tube of rigid plastics material between the two container parts, the flow opening being shut off with such a wall of the same plastics material. This barrier wall or dam is pierced prior to use by a suitably constructed opening means, as for example a spike so that the flow passage is produced between the two bag parts.

Lastly it is however also possible for the flow passage part to be blocked by a closure means, that owes its closing action in the passage to a frictional engagement and may for example be in the form of an elastic lug. Such a closure is more especially of value in a bag part subject to a certain internal gage pressure. In accordance with the invention the plug will be inserted, from the side of the container part that holds the bicarbonate solution, into the flow passage.

In place of a passage member of a rigid plastics, as for example polycarbonate or the like, it is also possible to use a passage member made of a soft plastics material, as for example soft PVC or polyethylene, that again is either closed with a frictionally retained closure member or is clamped in place by a clip means. Furthermore it is possible also to have a rigid plastics closure member that is integral or is kept in place by friction in the plastics closure member, such plastics closure member, as noted earlier, having a frangible break-off part, that is detached prior to mixing the two solutions.

It is more particularly preferred for a rigid tubular member to be integrally fused in place, its opening being joined with a frangible part along a line of weakness integrally as well. This closure member, herein referred to as a frangible member, is to be preferred in a twin-chamber bag structure, whose two chambers are present in one integrally constructed bag and are separated from each other by a weld seam, The frangible or break-off part is provided in this weld seam and so creates a flow passage between the two chambers after rupture or breaking off of the frangible part.

Such a twin-chamber bag is produced by welding two plastics foils along one outer edge so as to leave free filling slits and slits for the insertion of a discharge hose; in addition a weld seam is produced running transversely over the bag in order to divide the bag into first and second chambers, a flow passage member being inserted in this transversely running weld seam. The two solutions to be stored are filled into the bag chambers through the filling slits, in which if desired filling pipes may be welded. After such filling the filling slits or filling pipes are closed by welding, or in other words the insides of the chambers are sealed off from the outside atmosphere. Before doing this however a check will have been made to see that the discharge hose has been shut off as well.

The material of the bag will be an organic polymer having a low permeability to water vapor and carbon dioxide. Such polymers that may be used include polyethylene, polypropylene, PVC, polyvinylidene chloride, polymethyl methacrylate, and copolymers as for example ethylene/propylene plastics, poly-(ethylene/vinyl acetate), acrylonitrile/butadiene/styrene polymers, ethylene-propylene block copolymers, styrene copolymers and the like.

If PVC is utilized it is preferred for it only to contain plasticizers on an organic basis, as for example dioctyl phthalate.

Preferred bag materials that come into contact with the solutions are polyethylene and PVC.

In order to reduce permeability to water vapor and to carbon dioxide of the above listed polymers it is possible for the polymer used as the bag foil to have one or more layers in the form of a laminate component on its outer face having the effect of decreasing permeability. Such a laminate layer on the bag foil may for example be in the form of a metal foil or a further polymer, as for example polyamide, PVC, polyvinylidene chloride, polyvinyl fluoride, polytrifluorochloroethylene, polyethylene terphthalate, other polyesters or the like. It is preferred to employ polyamide, polyvinylidene chloride, polyethylene terphthalate and other polyesters.

The polymeric external and internal foils are preferably attached by a coating adhesive such as polyvinylidene chloride or polyurethane and after such bonding the laminate will be in a state ready for use.

At room temperature and at a relative humidity of approximately 85% preferred foils will as a rule have a permeability to water vapor, as ascertained in accordance with DIN 53,122,of under 1.

Such figures apply for standard foils with a thickness of 50 to 100 and more especially 75 microns, in the case of the internal foil, and 20 to 100 or more especially 30 to 70 microns, for the outer coating foil.

Furthermore in the case of preferred laminates the permeability of carbon dioxide is decreased to values under 20 cc/squ. meter per day per bar pressure difference.

It is more specially advantageous to use a laminating foil and a twin-foil bag produced therewith as described in generally in the German Offenlegungsschrift specification No. 3,200,263, such specification being incorporated by reference herein.

In accordance therewith the inner foil is a polyethylene one of medium to high density, that is normally produced by low pressure polymerisation. In this case the density will be in a range of 0.91 to 0.94 and will more especially have a value of 0.935 g/cc. Such polyethylene will readily withstand a sterilisation temperature of 115° to 125° C.

Furthermore this polyethylene is preferably coated with a polyamide foil with a thickness in the above mentioned ranges. Such foils are for example marketed by Sengewald of Halle/Westf., Western Germany under the trade name of "Flexovac V 7144", for medicinal purposes.

It is an advantage for this internal polyethylene foil to have an external hose of a copolymer of ethylene and vinyl acetate (EVA) welded into it, such external hose then subsequently being cross linked by means of high-energy radiation so that it will withstand, without loss of its elastic properties, the above mentioned sterilisation temperatures.

It is to be added that the flow passage member may be manufactured of cross-linked EVA inasfar as a flexible polymer is to be used for this purpose.

In keeping with a further embodiment of the invention it is possible to utilize a PVC in the form of standard medicinal bag material. Pieces of PVC hose may be employed in such a bag both as flow passage members and also as passage tubes or hoses and are welded in place.

Such internal PVC foil may, as noted hereinbefore, be coated with an outer foil to reduce permeability to water vapor and carbon dioxide, such outer foil being of a material as named above.

In keeping with further preferred embodiment of the invention, that is more particularly to be utilized with bag materials having a high permeability of carbon dioxide, the complete bag structure including the discharge duct and the connector joined to such discharge duct comprises a guard skin of a material with a very low permeability to carbon dioxide. This guard skin is advantageously made of a soft and transparent plastics, that is impermeable to microbes and furthermore will resist a sterilisation temperature of at least 115° to 125° C. Between this guard skin, that takes the place of the outer web of the above-noted laminate layer, and the bag structure of the present invention it is possible with advantage to have a gaseous carbon dioxide under such a pressure that the carbon dioxide partial pressure in the bicarbonate-containing solution is at least partly compensated or balanced thereby. This therefore inhibits decomposition of the bicarbonate. Such an arrangement is more particularly preferred in those cases in which a normal PVC bag, that has a wall thickness of about 0.4 to 0.6 mm, is used without any coating with an outer foil as a means for containing both fluids.

Such guard skins are preferably used in the form of laminates, as for example laminates of polyester and polypropolylene, polyamide and polypropylene or polyethylene terphthalate and polypropylene.

Such a guard skin consists of an upper web or sheet and a lower web, that are weld together at the edges to form a bag. If desired the one of the webs or both of them may be deep-drawn to be in accord with the form of the bag that is to be protected or covered as described in the European Pat. No. 50,255, which is incorporated herein by reference.

Furthermore inasfar as such a guard skin is made of a material with a very low permeability to carbon dioxide, it may be evacuated generally in keeping with the method of said European patent and thus brought into close contact with the bag to be protected. Consequently there is practically no gaseous carbon dioxide between the two bags.

Finally in place of laminates of plastics material it is possible to utilize a hybrid sheet composed of a plastics layer and a metallic foil, as for example aluminum foil, that in the thickness in which it tis used is practically impervious to to the carbon dioxide so that carbon dioxide diffusion is only possible at the places where the plastics is welded, such diffusion being generally negligible.

The volumetric filling capacities of the two bag parts are designed in accordance with the purpose of use, a preferred value being between 0.5 and 2.5 liters. In this respect the compartment made to accept the final mixture will be of such a size that the two fluids will both have sufficient room therein. On the other hand it is however feasible for the two fluids to be mixed with each other by squeezing on the bag and so pumping the fluids backwards and forwards between the compartments in the bag structure.

The acidic solution containing the calcium and magnesium salts may have the following composition expressed as mval (mEqu)l of water:

$Ca^{2+} = 1-10$
$Mg^{2+} = 0-6$
$Cl^- = 1-16$
$CH_3COOH = 4-6$

The bicarbonate-containing solution has the following components expressed in mval/l:

$Na^+ = 256-290$
$K^+ = 0-8$
$HCO_3^- = 56-75$
$Cl^- = 180-238$

In place of the sodium hydrogen carbonate in the bicarbonate-containing solution it is also possible to use sodium carbonate, the basic solution then having 120–128 mval/l of carbonate and the acidic solution having 60–64 mval/l of HCl.

The two solutions are mixed with each other in a ratio of 1 to 1, the final solution having the following composition expressed in mval/l:

$Ca^{2+} = 0.5-5$
$Mg^{2+} = 0-3$
$Cl^- = 90.5-121$
$CH_3COOH = 2-3$
$Na^+ = 128-145$
$K^+ = 0-4$
$HCO_3^- = 28-38$

The acetic acid present in the solution reacts with the hydrogen carbonate ion with the evolution of 2–3 mmol/l $CO_2$, that is physically dissolved in the mixture, a certain gage pressure resulting in the solution. This gage pressure is dependent on the partial pressure $p_{co2}$ and will be generally between 50 and 80 mm/Hg.

If sodium carbonate is used as a basically reacting agent, it will react with the hydrochloric acid of the acidic solution with the formation of $CO_2$ and hydrocarbonate ions in generally equal amounts. This amount of carbon dioxide may be held in the bag as well.

Because of its isotonic properties, such a solution may be used both for dialysis and for hemofiltration and furthermore for purposes of infusion.

In the event of the bicarbonate-containing solution being intended to be osmotically active in addition, as is normally the case for CAPD solutions, a certain amount of an osmotically active substance, as for example glucose, is contained in the acidic solution. In the present case the acidic solution will contain approximately 26 to 90 g of glucose/l, this giving on 1 to 1 dilution an osmolarity of the solution of approximately 350 to 550 mosm/l.

As a consequence of the strongly alkaline properties of a sodium carbonate solution and the pronounced evolution of carbon dioxide on reaction with the acidic solution, the use of sodium hydrogen carbonate is preferred to the use of sodium carbonate (soda).

It has been experienced as being particularly advantageous that, prior to mixing with the acid solution, the basic bicarbonate-containing solution, is held in that compartment which has the discharge duct or hose. This arrangement is to be preferred for safety reasons, since in the case of ambulant dialysis as undertaken by the patient him- or herself, there is in some cases a danger of the as yet unmixed solution passing through the discharge duct into the peritoneal cavity. A bicarbonate-containing solution in the unmixed condition may be tolerated by the patient without morbid symptoms, something that is not true of the acid one. For this reason it is preferred to have the bicarbonate solution in that compartment which is joined to the discharge duct. It is to be noted in this connection that prior art (see Ing et al. 1983) suggests filling of a single plastics bag with an acid solution, but this involves a risk.

An account of the invention will now be given using the working example to be seen in the figures.

FIG. 1 is a view of a bag from the side.

FIG. 2 is a section through the bag as taken on the line II—II of FIG. 1.

FIG. 3 is a view of the frangible part, placed between the two chambers of the bag, on a larger scale.

In FIGS. 1 and 2 a container 10 will be seen that is manufactured in the form of a plastics bag. This container 10 has two chambers, a first chamber 12 and a second one 14, that are divided from each other by a dividing structure in the form of a weld seam.

Furthermore the bag 10 has a welded marginal zone 18 by which the two chambers 12 and 14 are shut off from the atmosphere. This weld seam 18 furthermore joins with the weld seam 16 so that with the exception of the flow passage part 20, there is no flow communication between the chambers. This passage part 20 is set in the weld seam and surrounded thereby.

Furthermore the first chamber 12 is joined to a discharge duct 22 which preferably has the weld seam 18 formed round it and is capable of producing a connection with the first chamber if the closure means 24 (that is best designed to block the discharge duct 22) is opened. This means 24 will normally be made of a plastics tube with a frangible part thereon which is broken when the package is used.

The flow passage part 20, that is to be seen on a larger scale in FIG. 3, consists of a tubular part 26, that merges with a further tubular part 28 with a smaller external diameter and which is shut off by a frangible part 30 running along the line 32 of weakness.

The first chamber 12 is advantageously filled with a bicarbonate-containing fluid 34, yet to be diluted, whereas the second chamber 14 is filled with an acid solution 36. When the package is used the frangible part 30 is broken off from the flow passage part so that the acid solution 36 may make its way through the flow passage 38 into the flow passage part 20 and thence into the first chamber 12.

After the mixing of the two fluids and the production of the dialysing fluid or the fluid to be used for hemofiltration or the infusion fluid, the closure device 24 is opened to unblock the discharge duct 22. At its other end it is provided with a conventional connection means (not illustrated) as for example a CAPD connector, a catheter, an infusion device or the like.

Lastly, the container 10 has a suspension means 49 in the form of an eye welded onto its top end.

As has been described hereinbefore, the solutions are introduced through filling slits that are not shown in the welded edge 18 into the chambers 12 and 14 that are then closed by welding. If desired, even before such welding a certain amount of gaseous carbon dioxide is run into the chamber, as for example to produce an internal pressure of 40 to 80 mm/Hg and to influence the decomposition equilibrium of the bicarbonate.

Furthermore the container 10 may have an injection means (not shown) on the first chamber 12, as is usually the case with CAPD bags as presently used.

EXAMPLE

Containers 10 were produced holding 1500 ml of bicarbonate-containing solution in the first chamber 12, and 500 ml of acid solution in the second chamber 14, so that in all there were 2 liters of bicarbonate solution. Each such filled two liter package was then conventionally sterilized at approximately 120° C. and then stored for longer than 6 months. The unmixed solutions remained stable and their chemical composition did not alter. Investigations as to sterility, pyrogenes and particles, undertaken on the unmixed and mixed solutions were negative as well. Furthermore, the glucose added to the acid solution did not caramelize.

Lastly it is to be noted that the mixed solution remained stable 4 days after mixing.

The mixed solution had the following composition expressed in mval/l $Na^+$: 138

$K^+$: 1

$Ca^{2+}$: 4

$Mg^{2+}$: 1

$Cl^-$: 104

$HCO_3^-$: 35 acetate: 5

In addition the solution contained 16.5 g/l of glucose, this corresponding to an osmolarity of 369 mosm/l.

100 such packages were investigated whose mixed solutions had a mean pH value of 7.2 and mean carbon dioxide partial pressure ($p_{co2}$) of about 85 mm/Hg.

Four 2 liter containers were used for CAPD patients daily, whose treatment with such bicarbonate-containing solution was satisfactory.

We claim:

1. A container for preparing a bicarbonate-containing solution for dialysis, substitution or infusion for peritoneal dialysis, hemo filtration and the like comprising:
   (a) an outer bag structure of organic polymer having at least two chambers,
   (b) a first of said chambers filled with an aqueous solution containing carbonate,
   (c) a second of said chambers filled with an aqueous acid solution,
   (d) an openable flow blocking valve connecting said first with said second chamber, said valve being the sole ingress or egress means to said second chamber, and
   (e) at least one discharge tube fitted with a removable closure, said discharge tube passing through and being sealed to said outer bag and into a said first chamber.

2. A container for preparing a bicarbonate-containing solution for diaylsis, substitution or infusion for peritoneal dialysis, hemo filtration and the like comprising:
   (a) an outer bag structure of organic polymer having at least two chambers, (b) a first of said chambers filled with an aqueous solution containing bicarbonate, (c) a second of said chambers filled with an aqueous acid solution, (d) an openable flow blocking valve connecting said first with said second chamber, said valve being the sole ingress or egress means to said second chamber, and (e) at least one discharge tube fitted with a removable closure, said discharge tube passing through and being sealed to said outer bag and into a said first chamber.

3. A container in accordance with claim 2 wherein the total ionic strength of the solutions in said first chamber and in said second chamber when combined yield an isotonic solution.

4. A container in accordance with claim 3 wherein said second chamber additionally comprises an osmotically active substance in an amount sufficient to raise said isotonic solution to a higher predetermined osmolarity.

5. A container in accordance with claim 2 wherein the total alkalinity of the solution of said first chamber and the total acidity of the solution of said second chamber when combined yield a solution of physiological pH value that does not inhibit the natural defense mechanism of the peritoneum.

6. A container in accordance with claim 5 wherein the pH is approximately 7.2.

7. A container as claimed in claim 2 characterized in that the container is in the form of a twin-chamber bag whose first and second chambers are separated from each other by a dividing means.

8. A container as claimed in claim 7 characterized in that the dividing means is in the form of a weld seam running transversely across the bag and said blocking valve being a blocked passage through it able to be opened.

9. A container as claimed in claim 7 characterized in that the twin-chamber bag comprises an inner foil in the form of an organic polymer with a low permeability to water vapor and carbon dioxide.

10. A container as claimed in claim 9 characterized in that the inner foil is in the form of polyethylene or PVC.

11. A container as claimed in claim 9 characterized in that said inner foil is covered with an outer foil to form a laminate.

12. A container as claimed in claim 9 characterized in that the outer foil is a polyamide, PVC, polyvinylidene chloride, polyethylene terphthalate or other polyester.

13. A container as claimed in claim 12 characterized in that such laminate has a water vapor permeability of under 1 and has a maximum permeability for carbon dioxide of 20 cc/squ. meter per day per bar pressure difference, and the inner foil has a thickness of approximately 50 to 100 microns and the outer foil has a thickness of approximately 20 to 100 microns.

14. A container as claimed in claim 8 characterized in that the blocked passage has at least one tubular part of a hard resin, that is connected with a break-off part by way of a line of weakness.

15. A container as claimed in claim 2 characterized by a bag-like guard skin extending over the bag structure.

16. A container for preparing a bicarbonate-containing solution for dialysis, substitution or infusion for peritoneal dialysis, hemo filtration and the like comprising:

(a) an outer bag structure of organic polymer having at least two chambers, (b) a first of said chambers filled with an aqueous solution containing bicarbonate, (c) a second of said chambers filled with an aqueous acid solution, (d) an openable flow blocking valve connecting said first with said second chamber, said valve being the sole ingress or egress means to said second chamber, and (e) at least one discharge tube fitted with a removable closure, said discharge tube passing through and being sealed to said outer bag and into said first chamber, wherein the total ionic strength of the solutions in said first chamber and in said second chamber when combined yield an isotonic solution.

17. A container for preparing a bicarbonate-containing solution for dialysis, substitution or infusion for peritoneal dialysis, hemo filtration and the like comprising:

(a) an outer bag structure of organic polymer having at least two chambers, (b) a first of said chambers filled with an aqueous solution containing bicarbonate, (c) a second of said chambers filled with an aqueous acid solution, (d) an openable flow blocking valve connecting said first with said second chamber, said valve being the sole ingress or egress means to said second chamber, and (e) at least one discharge tube fitted with a removable closure, said discharge tube passing through and being sealed to said outer bag and into said first chamber, wherein the total alkalinity of the solution of said first chamber and the total acidity of the solution of said second chamber when combined yield a solution of physiological pH value that does not inhibit the natural defense mechanism of the peritoneum.

18. A container for preparing a bicarbonate-containing solution for dialysis, substitution or infusion for peritoneal dialysis, hemo filtration and the like comprising:

(a) an outer bag structure of organic polymer having at least two chambers, (b) a first of said chambers filled with an aqueous solution containing carbonate, (c) a second of said chambers filled with an aqueous acid solution, (d) an openable flow blocking valve connecting said first with said second chamber, said valve being the sole ingress or egress means to said second chamber, and (e) at least one discharge tube fitted with a removable closure, said discharge tube passing through and being sealed to said outer bag and into said first chamber, wherein the total ionic strength of the solutions in said first chamber and in said second chamber when combined yield an isotonic solution.

19. A container for preparing a bicarbonate-containing solution for dialysis, substitution or infusion for peritoneal dialysis, hemo filtration and the like comprising:

(a) an outer bag structure of organic polymer having at least two chambers, (b) a first of said chambers filled with an aqueous solution containing carbonate, (c) a second of said chambers filled with an aqueous acid solution,
(d) an openable flow blocking valve connecting said first with said second chamber, said valve being the sole ingress or egress means to said second chamber, and
(e) at least one discharge tube fitted with a removable closure, said discharge tube passing through and being sealed to said outer bag and into said first chamber, wherein the total alkalinity of the solution of said first chamber and the total acidity of the solution of said second chamber when combined yield a solution of physiological pH value that does not inhibit the natural defense mechanism of the peritoneum.

* * * * *